United States Patent
Salatka et al.

(10) Patent No.: US 6,564,804 B2
(45) Date of Patent: May 20, 2003

(54) FACE SHIELD AND FACE SHIELD SUPPORT ASSEMBLY

(76) Inventors: Robert G. Salatka, 457 Arden Dr., Encinitas, CA (US) 92024; William B. Buck, 2046 Coolngreen Way, Encinitas, CA (US) 92024

(*) Notice: Subject to any disclaimer, the term of this patent is extended or adjusted under 35 U.S.C. 154(b) by 0 days.

(21) Appl. No.: 09/818,185

(22) Filed: Mar. 26, 2001

(65) Prior Publication Data

US 2002/0134390 A1 Sep. 26, 2002

(51) Int. Cl.[7] ............................................. A61F 11/00
(52) U.S. Cl. ............................ 128/857; 2/9; 2/447; 2/452
(58) Field of Search ................................. 128/846, 857, 128/858; 2/8–9, 15, 424, 438, 441, 13, 426, 427, 457, 452; 341/41.44, 47–48, 55, 65, 71, 88, 103, 105, 124, 130–133, 148

(56) References Cited

U.S. PATENT DOCUMENTS

| | | | |
|---|---|---|---|
| 1,884,047 A | 10/1932 | McClellan | |
| 2,233,698 A | 3/1941 | Girouard | 2/206 |
| 2,342,982 A | 2/1944 | Stern et al. | 2/9 |
| 2,620,472 A | 12/1952 | Sors et al. | 2/13 |
| 2,774,970 A | 12/1956 | Du Bois | |
| 2,866,202 A | 12/1958 | Landis | 2/12 |
| 3,901,589 A | * 8/1975 | Bienenfeld | |
| 4,057,852 A | 11/1977 | Contant | 2/12 |
| 4,843,643 A | * 7/1989 | Parissenti et al. | 2/13 |
| 4,852,185 A | 8/1989 | Olson | 2/9 |
| 4,920,576 A | 5/1990 | Landis | 2/9 |
| 4,944,039 A | * 7/1990 | Dietrich | |
| 4,944,312 A | 7/1990 | Smith | 128/857 |
| 4,986,282 A | * 1/1991 | Stackhouse | 128/857 |
| D321,268 S | 10/1991 | Nix, Jr. | D29/16 |
| 5,113,529 A | 5/1992 | Carr | 2/13 |
| 5,170,502 A | * 12/1992 | Hegendorfer et al. | |
| 5,206,956 A | 5/1993 | Olson | 2/13 |
| 5,297,298 A | 3/1994 | Salatka et al. | 2/447 |
| 5,337,419 A | * 8/1994 | Russell | 2/9 |
| 5,416,923 A | 5/1995 | Peugh | 2/9 |
| 5,469,229 A | * 11/1995 | Greenbaum | 351/44 |
| 5,471,679 A | 12/1995 | Paoluccio | 2/9 |
| 5,666,664 A | 9/1997 | Hamilton | 2/13 |
| 5,692,522 A | 12/1997 | Landis | 128/857 |
| 5,862,530 A | 1/1999 | Shillington | 2/439 |
| 5,956,760 A | 9/1999 | Wine et al. | 2/9 |
| 6,016,808 A | 1/2000 | Landis | 128/857 |

* cited by examiner

Primary Examiner—Nicholas D. Lucchesi
Assistant Examiner—Lalita M Hamilton
(74) Attorney, Agent, or Firm—Knobbe, Martens, Olson & Bear, LLP

(57) ABSTRACT

A face shield support assembly comprises:
a frame member having a pair of resilient and biased memory-retaining temples at opposite ends and a face shield support member secured to the frame member having a pair of elbows spaced apart along the frame and a pair of protuberances each formed at an opposite end. One or more connection members secures the frame member to the face shield support member.

21 Claims, 5 Drawing Sheets

FACE SHIELD AND FACE SHIELD SUPPORT ASSEMBLY

BACKGROUND OF THE INVENTION

Face shields for protecting healthcare professionals from undesirable physical contact with debris or body fluids and exposure to virus and bacteria when attending to or operating on patients are well known. Such protective face shields are shown in U.S. Pat. Nos. 4,852,185 and 5,206,956. Other types of face shield devices are disclosed in U.S. Pat. Nos. 4,920,576 and 6,016,808. The present invention is directed to an improved disposable face shield which may be readily assembled and disassembled by the user and is comfortably worn without elastic or adjustable head straps.

SUMMARY OF THE INVENTION

The face shield of the present invention comprises a face shield support assembly to which a clear plastic face shield may be removably attached. The plastic face shield is provided with two pairs of holes joined by a slot or slit adjacent to the upper edge of the shield. The frame member supporting the plastic face shield is a lightweight one-piece design which may be conveniently and comfortably worn by the user.

DETAILED DESCRIPTION OF THE PREFERRED EMBODIMENTS

Figure 1:
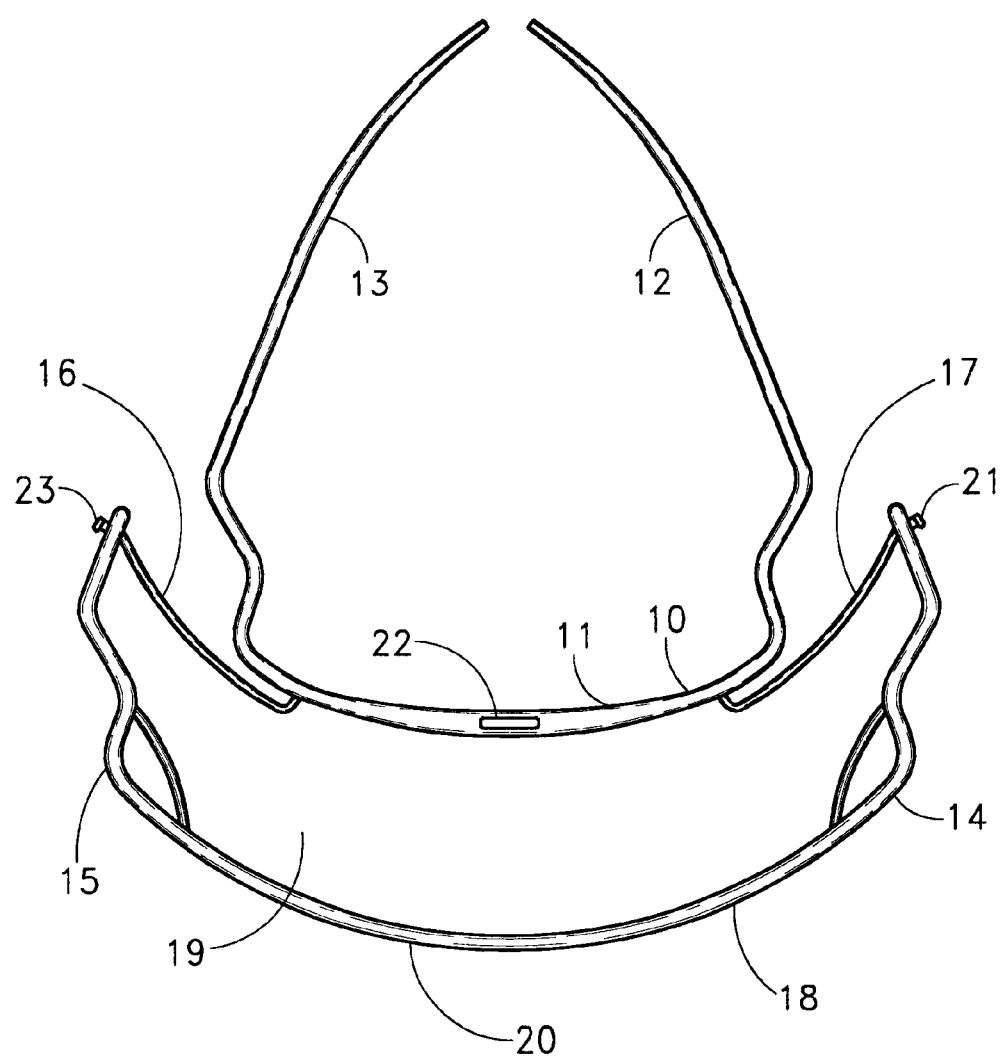
FIG. 1 is a top plan view of the face shield support assembly of the invention.
Figure 2:
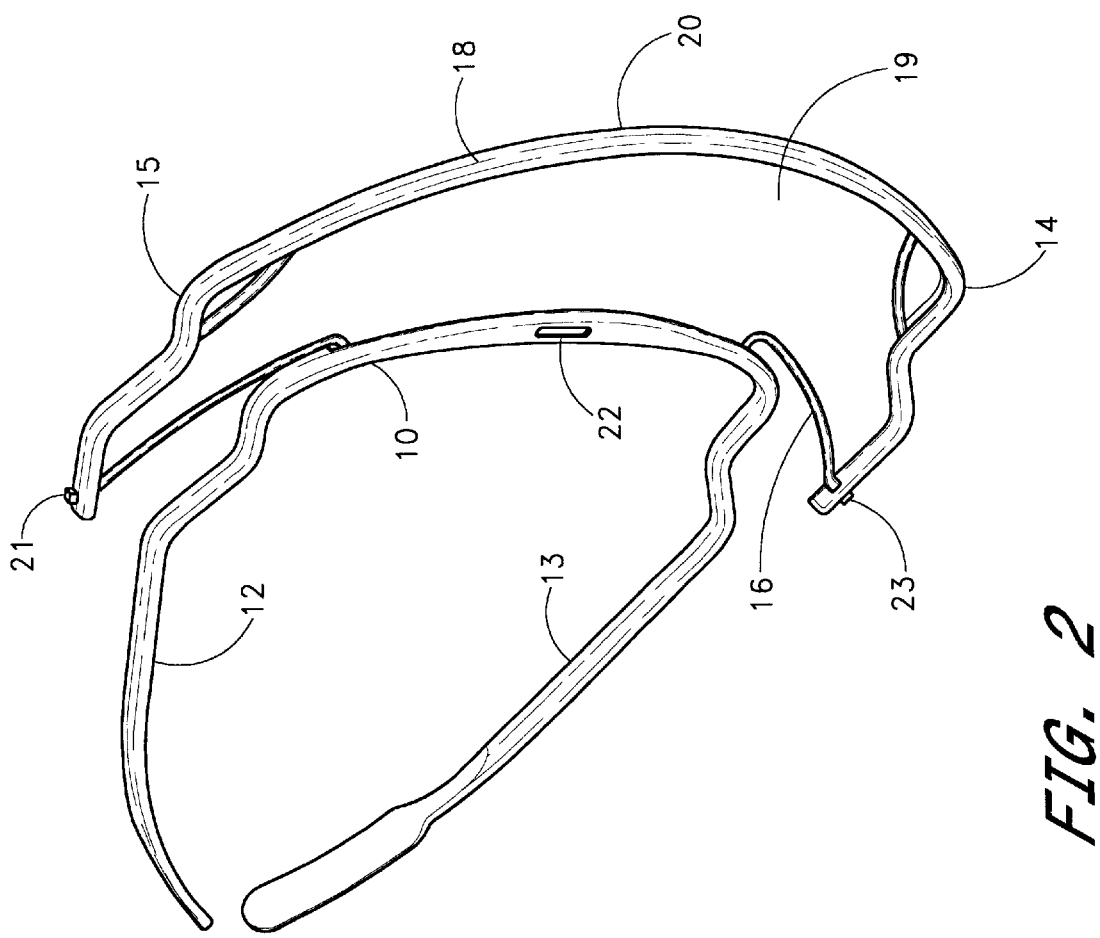
FIG. 2 is a perspective view of the underside of the face shield support assembly.

FIGS. 1 and 2 show the face shield support assembly of the invention. The support assembly includes a pair of resilient and biased memory-retaining temples 12 and 13 at opposite ends of frame member 10. A face shield support member 20 is secured to the frame member. The support member 20 comprises a pair of elbows 14 and 15 spaced apart along face shield support bar 18 with connection members or ribs 16 and 17 securing the frame member 10 to the face shield support member. A pair of buttons or protuberances 21 and 23 are formed at opposite ends of the support member 20. Although two ribs 16 and 17 are illustrated, any number of connection members may be used to secure the face shield support member 20 on the frame member 10. In a preferred embodiment, a generally opaque or light defusing or shading film or sheet 19 is positioned between ribs 16 and 17 and frame and face shield support members 10 and 20. Such a sheet 19 forms a visor which may be quite advantageous when the assembly is used in an operating room or otherwise where strong overhead light could be annoying and interfere with the vision of the user. In a preferred embodiment, sheet 19 is a rigid sheet integrated with and extending between the components thus forming part of the connection member for securing the frame member with the face shield support member for improving the structural integrity of the assembly.

The face shield support member 20 includes face shield support bar 18 and a pair of elbows 14 and 15 which are arched outwardly for securing the face shield as will be explained in more detail hereinafter. The bowed or curved shape of the face shield support bar 18 is also useful in forming the arched shape of the face shield as it rests against the support bar. The shape of the frame member is preferably curved or bowed along a forehead portion 11 which rests against a user's forehead when the face shield assembly is secured on a user's head. The temples 12 and 13 are integrally formed as part of the frame member so that the entire frame member is generally bowed along its length and biased toward an unsprung condition in which the ends are spaced apart a distance less than the width of a user's head. The temples are resilient and memory-retaining and biased toward one another so that when the face shield support assembly is placed on a user's head, the temples will be urged against the sides of the user's head for better holding the assembly and face shield in place. The temples will also lie above the user's ears much like eyeglass frame temples and with the forehead portion of the frame member resting comfortably against the user's forehead. The frame member is preferably formed of a light-weight spring-like plastic material, such as polyethylene, polypropylene or PVC, which retains its memory in an unsprung condition and which can be readily urged apart to further separate the temples 12 and 13 when the frame is placed on the user's head. Preferably, the face shield support member and connection means such as the ribs 16, 17 and rigid film 19 are also formed of the same material. More preferably, the entire assembly may be formed in a single molding operation to form an integral assembly comprising all of the different components.

Figure 3:
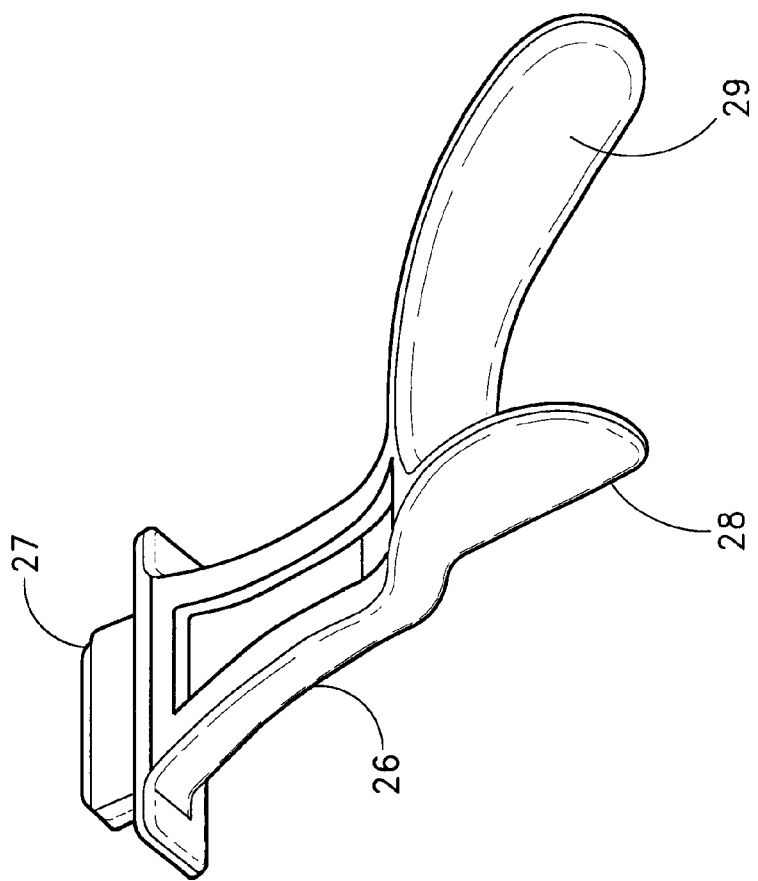
FIG. 3 is a perspective view of a removable nose bridge member.

FIG. 3 shows a nose bridge member 26 which may be removably secured to the face shield support assembly. The nose bridge member includes a flange 27 or similar component which may be inserted in a channel or notch 22 in the frame member. The flange 27 and notch 22 may be sized for a force fit, although a nipple or flange and detent or notch or other combination of snap fitting or mating components may be used instead for securing the nose bridge component on the frame member. The nose bridge member includes a pair of nose support pads 28 and 29 for resting along the user's nose bridge. The removable feature of the nose bridge member allows the face shield support assembly to be worn without the bridge member by a user also wearing a pair of eyeglasses, whereby the assembly is supported by the eyeglass frame.

Figure 4:
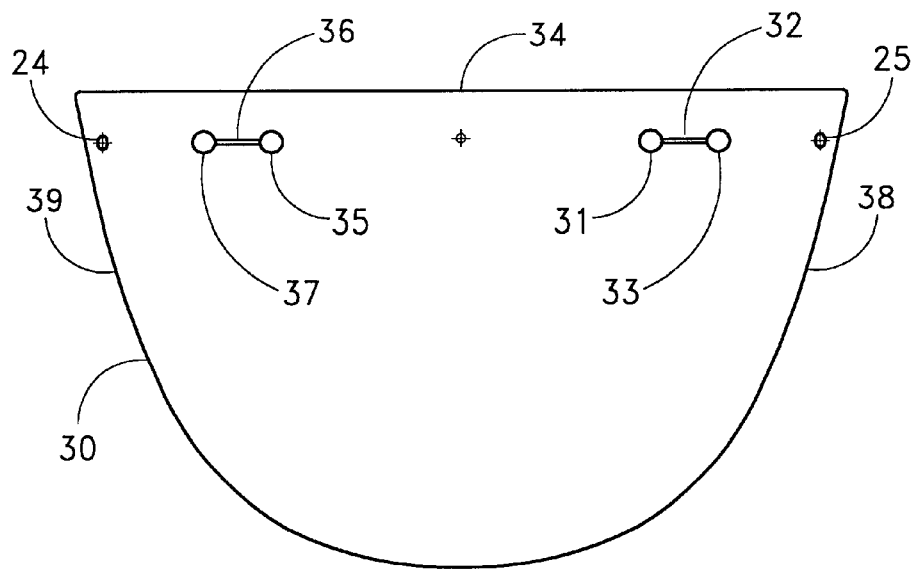
FIG. 4 is a plan view of a plastic face shield sheet for being secured to the face shield support assembly of the invention.

FIG. 4 illustrates a face shield member comprising a clear plastic film or sheet 30 having opposite side edges 38 and 39 and a upper edge 34. The shape of the face shield is not critical, but should be long enough and wide enough to adequately cover the user's face, preferably below the chin when the assembly is worn. The upper edge 34 is also preferably substantially linear and extending generally parallel to the face shield support bar 18.

Figure 5:
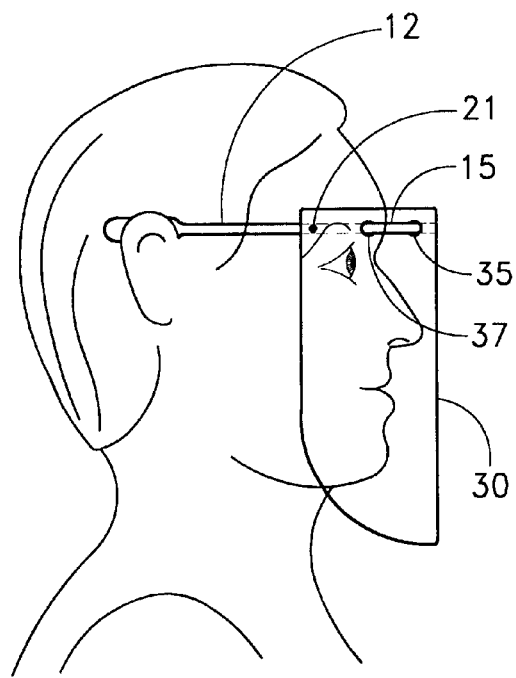
FIG. 5 is a side view of the assembled face shield of the invention.

Another feature of the face shield is the manner in which it is secured to the face shield support member. For this purpose, the face shield uses two pairs of two holes, each pair of holes being spaced apart on opposite sides of the face shield and adjacent to the upper edge 34. Each pair of holes is separated by a slot or slit which extends between the pair of holes. As shown, first pair of holes 31 and 33 is separated by a slot 32 and a second pair of holes 35 and 37 separated by a slot 36. Each pair of holes and slot are preferably substantially parallel with the upper edge 34 of the face shield although a somewhat angled slot may also be used. In assembling the device, the holes and slots are used to secure the face shield to the support member by forcing the elbows of the support member through the slots so that each elbow extends outwardly through a slot and through each of the holes. FIG. 5 illustrates elbow 15 extending through holes 35 and 37 and through slot 36. Although a slit may be used extending between the pair of holes instead of a slot, a wider slot allows the elbow to be pushed more easily through the face shield when it is secured on the support member. However, the width of the slot should not be greater than the diameter of the holes, and is preferably less than such diameter to provide more secure fastening of the face shield on the support member. The face shield also incorporates openings 24 and 25 adjacent to opposite upper corners of the plastic sheet between the upper edge 34 and side edges. The openings may be formed by small slits in the plastic, or by holes sized to force fit a protuberance. The openings are used for securing the corners of the face shield on protuberances 21 and 23 at each end of the face shield support member by simply forcing or snapping the protuberances through the respective holes or openings.

Although the face shield support member 20 is shown as terminating at opposite ends, it may also be integrated with the frame member 10 by extending the ends of the support members into or integral with the frame member. Where such structure is used, the ends of the face shield support member become or act as connection members or ribs for securing the support member to the frame member. Thus, such a structure may be used instead of or in addition to the use of other connection members or ribs. Accordingly, it is to be understood that the shape of the connection members 16 and 17 as shown is illustrative only.

Figure 6:
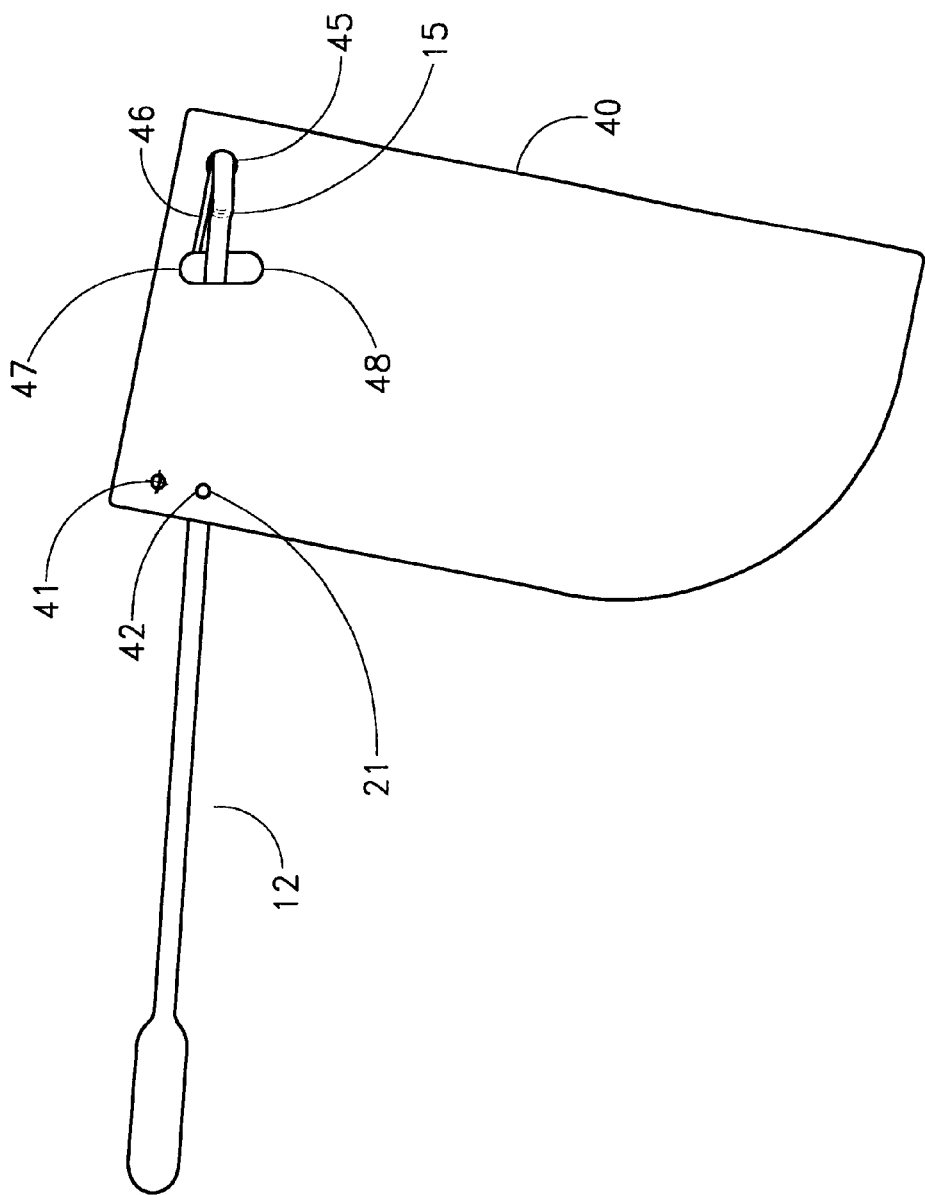
FIG. 6 is a side view of the face shield assembly showing another face shield embodiment.

The face shield may also be formed or provided with features allowing it to be tilted or slanted more or less relative to the plane of the user's face. An example of such a modification is illustrated in the embodiment shown in FIG. 6 in which face shield 40 is provided with holes 45 and 47 separated by slot 46, and a channel or slot 48 extending downwardly from hole 47 generally normal to slot 46. A second opening 42 adjacent to the side edge is located below opening 41. Substantially identical features are located on the opposite side of the face shield. In the embodiment shown elbow 15 extends from channel 48 below hole 47 and the face shield has been secured on protuberance 21 through opening 42. By attaching the face shield to the frame member at an angle shown in FIG. 6, the face shield is slanted so that it is positioned somewhat closer to the user's face as compared to the embodiment shown in FIG. 5. Such a feature may be more advantageous for certain uses or preferred by some users. Any number of openings may be formed along the side edge for securing the protuberances allowing for a choice of angles of the face shield relative to the user's face. Other modifications and features of the assembly within the purview of the invention will be evident to those skilled in the art.

What is claimed is:

1. An integrally formed face shield support assembly comprising:
a frame member for being worn on a user's head comprising a forehead portion for resting against a user's forehead having a pair of integral resilient and biased temples at opposite ends thereof and an integral face shield support member secured to said frame member and having a pair of elbows spaced apart therealong and a pair of protuberances, each formed at an opposite end thereof, and one or more integral connection members secured to said frame member and said face shield support member.

2. An assembly of claim 1 wherein said one or more connection members comprises a plurality of ribs extending between said frame member and said face shield support member.

3. An assembly of claim 1 wherein said one or more connection members comprises a substantially rigid sheet or film secured to said frame member and said face shield support member.

4. An assembly of claim 2 wherein said one or more connection members include a substantially rigid sheet or film extending between said frame member and said face shield support member.

5. An assembly of claim 1 or 2 including a generally opaque or light diffusing or shading film secured between said frame member and said face shield support member.

6. An assembly of claim 1, 2 or 3 wherein said frame member comprises an elongated flexible shaft generally bowed along its length between opposite ends thereof and biased toward a first unsprung condition having said opposite ends spaced apart a distance less than the user's head between the ears.

7. An assembly of claim 6 wherein said face shield support member comprises a support bar.

8. An assembly of claim 7 including a nose bridge support member removably secured to said frame member.

9. An assembly of claim 6 including a nose bridge support member removably secured to said frame member.

10. An assembly of claim 6 including a substantially clear plastic face shield removably secured to said face shield support member.

11. An assembly of claim 10 wherein said face shield comprises a plastic film or sheet having an upper edge and opposite side edges, and two pairs of holes spaced apart on opposite sides of said sheet, each pair of holes comprising a first hole and a second hole, each of the holes positioned along a plane adjacent to an generally parallel with said upper edge and film or sheet having a substantially straight slit or slot extending between the holes of each pair of holes.

12. An assembly of claim 11 wherein said upper edge extends substantially parallel with said plane.

13. An assembly of claim 11 wherein said slits or slots extend substantially parallel with said plane.

14. An assembly of claim 11 wherein said plastic film or sheet includes an opening adjacent to each side edge, each opening having a different protuberance secured therein.

15. An assembly of claim 10 wherein said face shield comprises a plastic film or sheet having an upper edge and opposite side edges, and a pair of substantially straight coplanar slots, each having a different elbow secured therein.

16. An assembly of claim 15 wherein said plastic film or sheet includes an opening adjacent each side edge, each opening having a different protuberance secured therein.

17. An assembly of claim 15 or 16 wherein said plastic film or sheet includes an opening adjacent each side edge, each hole having a different protuberance secured therein.

18. An assembly of claim 11 wherein a first hole is closer to a side edge of said plastic film or sheet than a second hole of each of said pair, and having a channel extending downwardly from each first hole for receiving an elbow therethrough, and a plurality of openings extending along each said side edge for receiving a protuberance therethrough.

19. An assembly of claim 1, 2 or 3 wherein said face shield support member comprises a support bar.

20. An assembly of claim 1, 2 or 3 including a nose bridge support member removably secured to said frame member.

21. An assembly of claim 1, 2 or 3 including a substantially clear plastic face shield removably secured to said face shield support member.

* * * * *